United States Patent
Takahashi

(10) Patent No.: US 8,282,881 B2
(45) Date of Patent: Oct. 9, 2012

(54) ANALYTE TREATMENT APPARATUS

(75) Inventor: Kenji Takahashi, Chikuma (JP)

(73) Assignees: Sakura Seiki Co., Ltd., Nagano (JP); Sakura Finetek Japan Co., Ltd., Tokyo (JP)

( * ) Notice: Subject to any disclaimer, the term of this patent is extended or adjusted under 35 U.S.C. 154(b) by 319 days.

(21) Appl. No.: 12/668,014

(22) PCT Filed: Jul. 3, 2008

(86) PCT No.: PCT/JP2008/062084
§ 371 (c)(1),
(2), (4) Date: Jan. 6, 2010

(87) PCT Pub. No.: WO2009/008331
PCT Pub. Date: Jan. 15, 2009

(65) Prior Publication Data
US 2011/0003373 A1    Jan. 6, 2011

(30) Foreign Application Priority Data
Jul. 11, 2007 (JP) .................... 2007-182138

(51) Int. Cl.
*G01N 21/00* (2006.01)
(52) U.S. Cl. ..................... 422/82.05; 422/82.09; 422/63; 422/68.1; 422/400; 422/401; 435/288.71
(58) Field of Classification Search .......... 422/400–401, 422/82.05, 547, 565, 63, 68.1, 82.09
See application file for complete search history.

(56) References Cited

U.S. PATENT DOCUMENTS
6,197,576 B1 * 3/2001 Eden .................... 435/288.7
2006/0127277 A1 * 6/2006 Numajiri .................... 422/65

FOREIGN PATENT DOCUMENTS
| JP | U63-97840 A | 6/1988 |
| JP | U2-135848 A | 11/1990 |
| JP | 2000-346767 | 6/1999 |
| JP | 2005-088558 | 4/2005 |

OTHER PUBLICATIONS

International Search Report dated Jul. 29, 2008 for PCT/JP2008/062084.

* cited by examiner

*Primary Examiner* — Brian R Gordon
(74) *Attorney, Agent, or Firm* — Blakely Sokoloff Taylor & Zafman LLP

(57) ABSTRACT

An analyte treatment apparatus comprising liquid chemical tanks storing liquid chemicals; and a treatment unit carrying out a treatment by supplying the liquid chemicals, so as to facilitate observation. The liquid chemical tanks are made of resin and housed inside a housing unit. Openings are formed in the housing unit. Light projecting means is provided outside of the treatment unit and projects light into each liquid chemical tank through the opening of the housing unit. A colored transparent door is provided to the housing unit and located at the other side with respect to a specific side of the liquid chemical tanks from which light diffusely reflected at the one side and the opposite side of the liquid chemical tank or in the liquid chemical tank can be visually checked, so as to visually check the reflected light. A control unit controls ON-OFF switching of the light projecting means.

7 Claims, 7 Drawing Sheets

ANALYTE TREATMENT APPARATUS

This is a non-provisional application claiming the benefit of International Application No. PCT/JP2008/062084, filed Jul. 3, 2008.

FIELD

The present invention relates to an analyte treatment apparatus and in more detail, to an analyte treatment apparatus that successively supplies a variety of liquid chemicals, which are separately stored in a plurality of liquid chemical tanks made of resin, to a treatment unit in which an analyte collected from an organism has been placed and carries out treatment to facilitate observation of the analyte.

BACKGROUND

Treatment that facilitates observation of an analyte collected from an organism such as a human body or an animal, as one example, fabricating a microscope specimen from a tissue fragment as an analyte collected from an organism such as a human body or an animal, is carried out as disclosed in Patent Document 1 listed below using a tissue fragment treatment apparatus 10 depicted in FIG. 6. In the tissue fragment treatment apparatus 10, a variety of treatments such as fixing, dewatering, degreasing/substitution, and paraffin embedding are carried out on a tissue fragment held in a treatment tank 12. During such treatments, a variety of liquid chemicals such as formalin, alcohol, xylene, and paraffin are successively supplied into the treatment tank 12 in which the tissue fragment is held.

Out of such liquid chemicals, formalin, alcohol, and xylene are normally stored separately in rectangular liquid chemical tanks that are made of resin and are housed inside a tank housing unit 14 of the tissue fragment treatment apparatus 10. The tank housing unit 14 is equipped with a transparent door 14a. On the other hand, since paraffin is solid at room temperature, it is customary to house a paraffin container for storing paraffin inside a paraffin housing unit 16 that is formed separately to the tank housing unit 14 and is kept at a predetermined temperature. Predetermined liquid chemicals are successively supplied into the treatment tank 12 from the liquid chemical tanks that store the various chemicals and from the paraffin container according to signals from a control unit 18.

Settings of the control unit 18 can be made via a ten key pad 20 provided on a panel, and information such as the result of a setting operation can be monitored via a monitor unit 22.
Patent Document 1
 Japanese Laid-Open Patent Publication No. 2000-346767

In the tissue fragment treatment apparatus 10 depicted in FIG. 6, the rectangular liquid chemical tanks that store the various liquid chemicals such as formalin, alcohol, and xylene are housed inside the tank housing unit 14 as depicted in FIG. 7. A plurality of liquid chemical tanks 24 are housed on three levels inside the tank housing unit 14. Connection sockets 30a for connecting to connection openings of the liquid chemical tanks 24 are attached to a partition plate 42 of the tank housing unit 14 and the connection sockets 30a are connected by delivery pipes 28 to the treatment tank 12. Control valves (not shown) are provided on the delivery pipes 28 that connect the individual liquid chemical tanks 24 and the treatment tank 12. The control valves are opened and closed according to signals from the control unit 18 (see FIG. 6) to supply the liquid chemicals inside the liquid chemical tanks 24 to the treatment tank 12. The connection openings of the liquid chemical tanks 24 that are held on the same level are covered by a waste gas header 30 so as to collect gasified chemicals that leak from the connection openings of the liquid chemical tanks 24. Out of the waste gas headers 30 provided on the different levels, the waste gas header 30 on the top level is connected by a connection pipe 32 to the waste gas header 30 on the middle level, and the waste gas header 30 on the middle level is connected by a connection pipe 32 to the waste gas header 30 on the bottom level. The waste gas header 30 on the bottom level is connected by a waste gas pipe 34 to a waste gas processing unit 36 in which an adsorbent such as activated charcoal is held, so that gasified chemicals that have not condensed in the waste gas headers 30 will be absorbed by the waste gas processing unit 36. On the other hand, condensed liquid 40 that has condensed in the waste gas headers 30 is collected in the bottom waste gas header 30 and is stored in a waste liquid tank 38. However, the liquid chemicals stored separately in the liquid chemical tanks 24 housed inside the tank housing unit 14 of the tissue fragment treatment apparatus 10 will need to be replaced with new chemicals or refilled depending on factors such as the remaining amount of chemical or changes in concentration that occur during the processes of the tissue fragment treatment. To do so, it is necessary to disconnect the connection opening of a liquid chemical tank 24 from the waste gas header 30 and remove the liquid chemical tank 24 from the tank housing unit 14. In addition, it is also necessary to insert the liquid chemical tank 24 with new liquid chemical inside the tank housing unit 14 and to reconnect the connection opening of the liquid chemical tank 24 and the waste gas header 30. The act of disconnecting and reconnecting the connection openings of the liquid chemical tanks 24 and the waste gas headers 30 should be easy to carry out, and as depicted in FIG. 8, Patent Document 1 mentioned above proposes connecting the connection plugs 24a of the liquid chemical tanks 24 and the connection sockets 30a provided on the waste gas headers 30 via a one-touch operation.

SUMMARY

According to the tissue fragment treatment apparatus 10 depicted in FIGS. 6 to 8 and proposed in Patent Document 1, the connection plugs 24a of the liquid chemical tanks 24 and the connection sockets 30a can be connected by a one-touch operation, which facilitates operations such as replacing the liquid chemicals stored in the liquid chemical tanks 24.

However, in the tissue fragment treatment apparatus 10 depicted in FIGS. 6 to 8, it is customary to insert a plurality of tissue fragments inside the treatment tank 12 and to carry out a treatment for a long period according to automatic operation. When doing so, aside from occasional monitoring of the operational state of the tissue fragment treatment apparatus 10, the tissue fragment treatment apparatus 10 will generally operate automatically without human intervention.

To enable the tissue fragment treatment apparatus 10 to successfully complete the treatment on the plurality of tissue fragments inserted into the treatment tank 12 by automatic operation in this way for a long period without human intervention, it is important to check whether predetermined amounts of predetermined types of liquid chemicals are stored in advance in the liquid chemical tanks 24 housed inside the tank housing unit 14. This is because there is the risk of the treatment being invalid if the treatment has been carried out without a predetermined liquid chemical being used. In addition, if the amount of a particular liquid chemical is insufficient, the treatment that uses such chemical will not be completed, and to prevent the tissue fragment from drying out, a liquid chemical will be introduced into the treatment tank 12 from another tank and the apparatus will enter a halted state.

If the tissue fragment treatment apparatus 10 has halted in this way, it will be necessary to restart operation after refilling the liquid chemical whose amount was insufficient, and the time spent in the halted state will be lost. This means that there is the risk of the treatment of a tissue fragment not finishing within the predetermined time and affecting subsequent operations.

There is also the risk that when the tissue fragment treatment apparatus 10 has spent a long time in the halted state in a condition where the amount of liquid chemical filling the treatment tank 12 is insufficient, the tissue fragment will no longer be usable for microscopy.

In addition, as the number of uses increases for a liquid chemical that is used in multiple treatments, there is the risk of constituents of the tissue fragment becoming mixed into the liquid chemical, of an increasing proportion of other liquid chemicals becoming mixed in, of the liquid chemical becoming sullied, and/or of the concentration of the liquid chemical itself falling, all of which can adversely affect the quality of the treated tissue fragment.

Liquid chemical tanks that are made of resin are normally used as the liquid chemical tanks 24 used in the tissue fragment treatment apparatus 10.

On the other hand, organic solvents such as formalin and xylene are used as the liquid chemicals stored in the liquid chemical tanks 24. For this reason, to improve the solvent resistance of the liquid chemical tanks 24, thick-walled liquid chemical tanks 24 made of crystalline resin are used as the liquid chemical tanks 24 made of resin that store organic solvents such as xylene. For this reason, the entire resin walls of the liquid chemical tanks 24 become cloudy and opaque, making it difficult to visually check the amount of liquid chemical stored in each liquid chemical tank 24 from outside the liquid chemical tanks 24. In particular, the amount of a liquid chemical that has been used multiple times and has been become cloudy due to the mixing in of constituents and the like of the tissue fragment will be even more difficult to visually check from outside an opaque liquid chemical tank 24.

It will also be difficult to visually check changes in the extent to which a cloudy liquid chemical has become sullied by the mixing in of constituents and the like of the tissue fragment.

It is an object of the present invention to provide an analyte treatment apparatus that solves the problem with a conventional analyte treatment apparatus equipped with liquid chemical tanks that are made of resin whereby it is difficult to easily visually check the amount and the like of a stored liquid chemical from outside, that enables the amount of liquid chemical and the extent of sullying of a liquid chemical stored in a liquid chemical tank made of resin to be easily checked from outside the liquid chemical tank, and is capable of preventing operation from being halted due to an insufficient amount of liquid chemical during treatment of an analyte, thereby preventing a fall in the quality of the treated analyte.

By extensively investigating the problem described above, the present inventor found that even with a thick-walled liquid chemical tank made of resin where it is difficult to visually check the amount of stored liquid chemical from outside, if light is projected from one side of the liquid chemical tank, it will definitely be possible to visually check the amount of stored liquid chemical from another side of the liquid chemical tank. By doing so, the present invention was reached.

That is, the present invention is an analyte treatment apparatus that successively supplies a variety of liquid chemicals individually stored in a plurality of liquid chemical tanks made of resin to a treatment unit, in which an analyte collected from an organism has been placed, and carries out a treatment to facilitate observation of the analyte, wherein the analyte treatment apparatus includes light projecting means on one side of the liquid chemical tanks so that light is projected into each liquid chemical tank from at least one side surface thereof and the light that has passed through a resin wall of the liquid chemical tank is diffusely reflected inside the liquid chemical stored inside the liquid chemical tank, thereby enabling various information about the liquid chemical to be known from another side of the liquid chemical tank.

The analyte treatment apparatus according to the present invention can be favorably applied to a tissue fragment treatment apparatus that successively supplies the variety of liquid chemicals individually stored in the plurality of liquid chemical tanks made of resin to a treatment tank in which a tissue fragment for use as a microscope sample has been inserted.

By providing the light projecting means separately for the plurality of liquid chemical tanks, it is possible to visually check a variety of information about liquid chemicals separately stored in the respective liquid chemical tanks easily from outside the liquid chemical tanks, which makes it easy to manage the amounts of liquid chemicals separately stored in the liquid chemical tanks. If light-emitting diodes are used as the light projecting means, it is possible to miniaturize and extend the working life of the light projecting means. In addition, it is possible to increase the brightness of the light projecting means and further improve the contrast between the liquid chemical tanks and the stored liquid chemicals.

In addition, by using a variable color light projecting means capable of changing a color of emitted light as the light projecting means provided on one side of the plurality of liquid chemical tanks and providing a control unit that controls the color of the emitted light of the variable color light projecting means, it is possible for example to illuminate a group of liquid chemical tanks that store the same liquid chemical with light of the same color and liquid chemical tanks that store different liquid chemicals with light of respectively different colors, which makes it possible to manage various information about the liquid chemicals on a chemical-by-chemical basis. It is also possible for the user to check the connected state of the respective liquid chemical tanks and to reliably and easily know whether there is a liquid chemical tank that has exceeded a limit on the number of uses. By constructing the variable color light projecting means of at least two of a red light-emitting diode, a green light-emitting diode, and a blue light-emitting diode, it is possible to combine such light-emitting diodes and use projected light of a variety of colors, thereby achieving a variable color light projecting means that has high brightness and is miniaturized.

In addition, by housing the plurality of liquid chemical tanks inside a housing unit equipped with a door and using a colored transparent door as the door on the other side of the liquid chemical tanks housed in the housing unit, it is possible to further improve the contrast between the liquid chemical tanks and the stored liquid chemicals in a state where the door is closed and therefore possible to check various information about the liquid chemicals separately stored in the liquid chemical tanks.

Note that by placing a float that blocks the light from the light projecting means inside the liquid chemical tanks, it is possible to visually check properties such as the specific gravity of the liquid chemicals from outside the liquid chemical tanks and to manage the amounts and concentrations of the liquid chemicals.

EFFECT OF THE INVENTION

With the analyte treatment apparatus according to the present invention, light that is projected from one side of liquid chemical tanks made of resin is diffusely reflected within the liquid chemicals stored inside the liquid chemical tanks, resulting in the entire liquid chemicals that are stored becoming brighter, which improves the contrast between the liquid chemicals and the liquid chemical tanks.

This means that it is possible to visually check the surface of the liquid chemicals stored in the liquid chemical tanks from the other side of the liquid chemical tanks, which makes it possible to grasp the stored amount of liquid chemicals stored inside the liquid chemical tanks.

Accordingly, if the stored amount of a liquid chemical inside a liquid chemical tank is low and there is the possibility of the amount of liquid chemical becoming insufficient within the predicted operating period of the analyte treatment apparatus, it is possible to take action such as adding liquid chemical to the liquid chemical tank or replacing the tank with a liquid chemical tank that stores a predetermined amount of the liquid chemical. As a result, it is possible to prevent from the outset a situation where the analyte treatment apparatus halts during operation due to insufficient liquid chemicals, which improves the reliability of the apparatus.

Also, even with a liquid chemical where the contrast with the liquid chemical tank is favorable for the projected light, once the chemical has been used multiple times in analyte treatments, the chemical will become cloudy due to constituents and the like of the analyte becoming mixed into the chemical, resulting in a fall in the contrast between the liquid chemical tank and the liquid chemical for the projected light. From the extent to which the contrast between the liquid chemical tank and the liquid chemical has fallen, the user can easily know the usage limit of a liquid chemical, and by taking appropriate action such as replacing the liquid chemical, it is possible to favorably maintain the quality of the treated analyte.

BEST MODE FOR CARRYING OUT THE INVENTION

Figure 6:
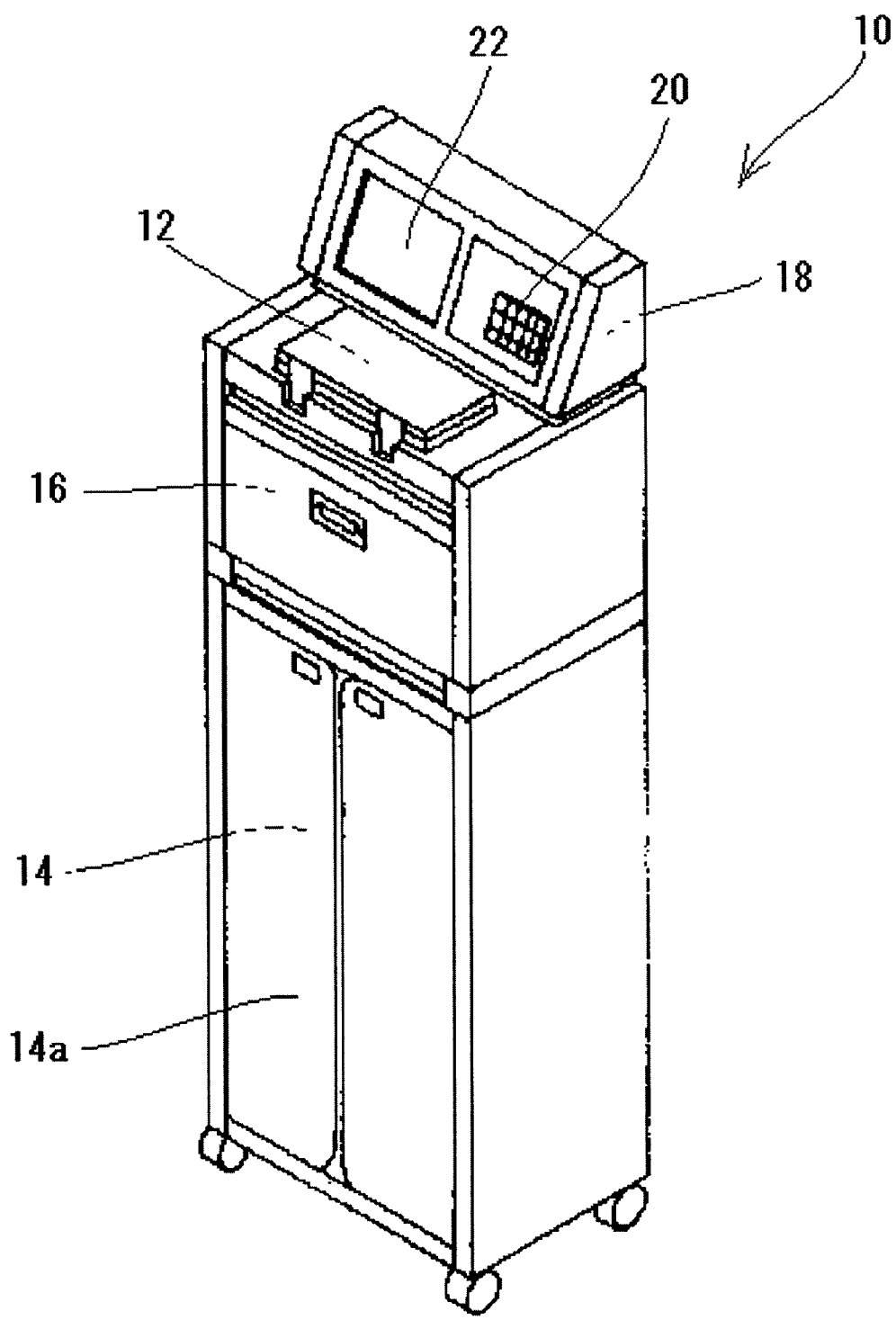
FIG. 6 is a perspective view useful in explaining the external appearance of the tissue fragment treatment apparatus.
Figure 7:
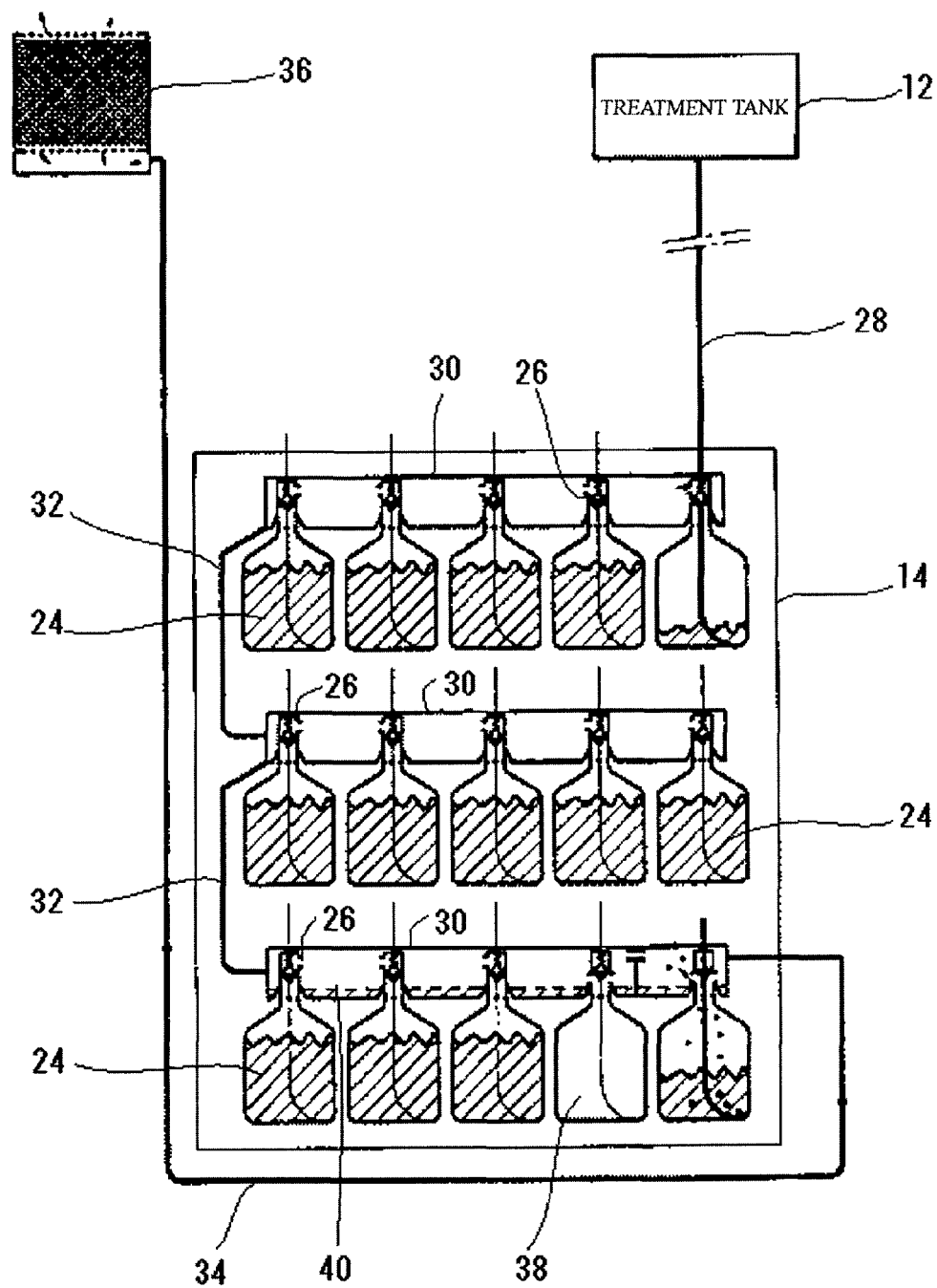
FIG. 7 is a schematic diagram useful in explaining the overall construction of the tissue fragment treatment apparatus depicted in FIG. 6.
Figure 8:
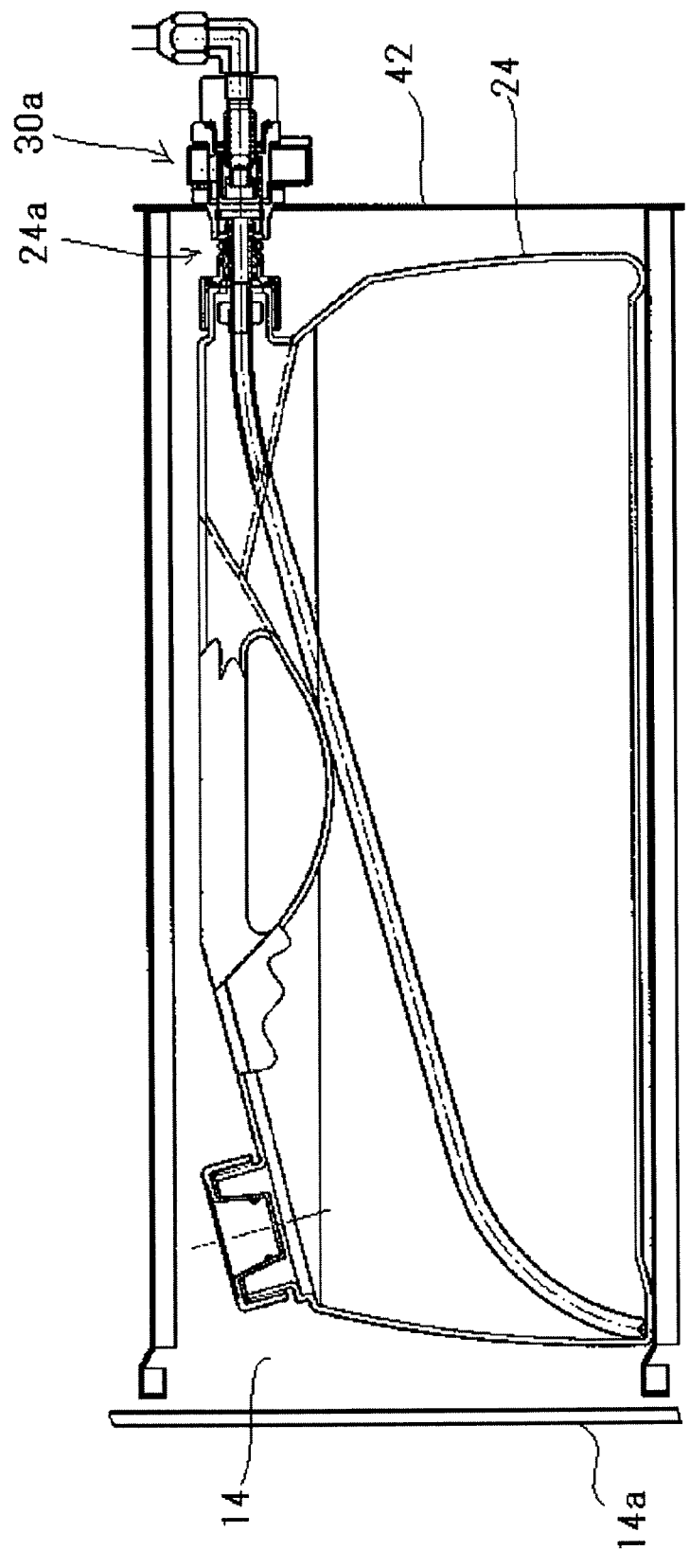
FIG. 8 is a partial cross-sectional view useful in explaining the construction of a connection plug provided on a conventional liquid chemical tank and a connection socket fixed to a rear plate.

Since the appearance of a tissue fragment treatment apparatus as an analyte treatment apparatus according to the present invention is substantially the same as the tissue fragment treatment apparatus depicted in FIG. 6, detailed description thereof is omitted. Also, as depicted in FIG. 7, the liquid chemical tanks 24 that are made of resin, are rectangular in shape, and store various liquid chemicals such as formalin, alcohol, and xylene in advance are housed inside the tank housing unit 14 depicted in FIG. 6 (i.e., since the overall construction of the tissue fragment treatment apparatus according to the present invention is the same as in FIG. 7, detailed description thereof is omitted).

Figure 1:
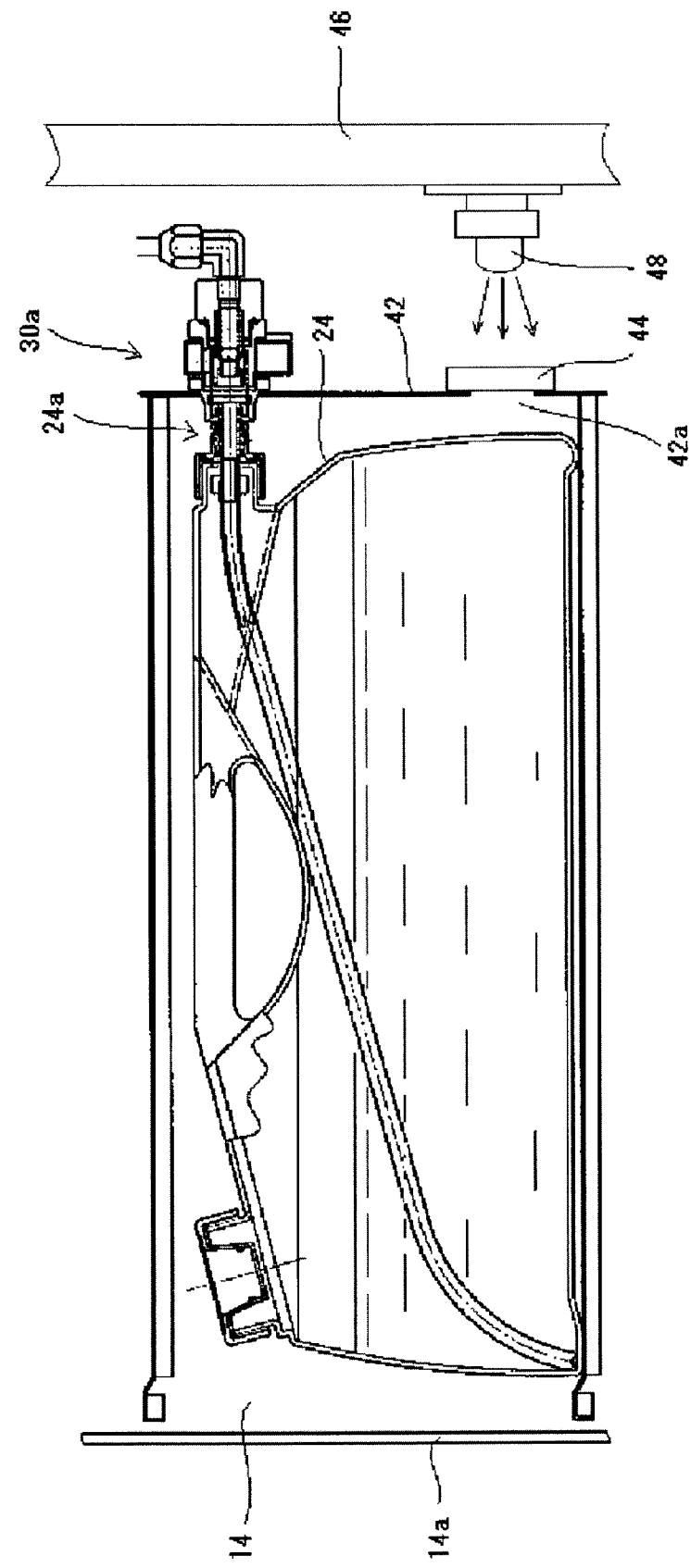
FIG. 1 is a partial cross-sectional view of a tissue fragment treatment apparatus as an analyte treatment apparatus according to the present invention.

As depicted in FIG. 1, the connection plug 24a provided on the other side ("one side" for the present invention) of the liquid chemical tank 24 housed inside the tank housing unit 14 to a door 14a ("another side" for the present invention) is connected by a one-touch operation to the connection socket 30a. The connection socket 30a is fixed to a center partition plate 42 of the tank housing unit 14.

Openings 42a are formed in the center partition plate 42 at positions corresponding to positions near the bottom of the liquid chemical tanks 24, and are covered by transparent plates 44.

In addition, as depicted in FIG. 1, light projecting means is provided, at positions corresponding to the transparent plates 44, on an inner wall surface of a rear plate 46 that is positioned outside a center partition plate 42 and forms the rear of the tank housing unit 14. As the light projecting means, it is possible to use a variety of light emitting apparatuses such as incandescent lamps, fluorescent lamps, or light-emitting diodes. In the analyte treatment apparatus depicted in FIG. 1, light-emitting diodes 48 are provided as the light projecting means.

Figure 2:
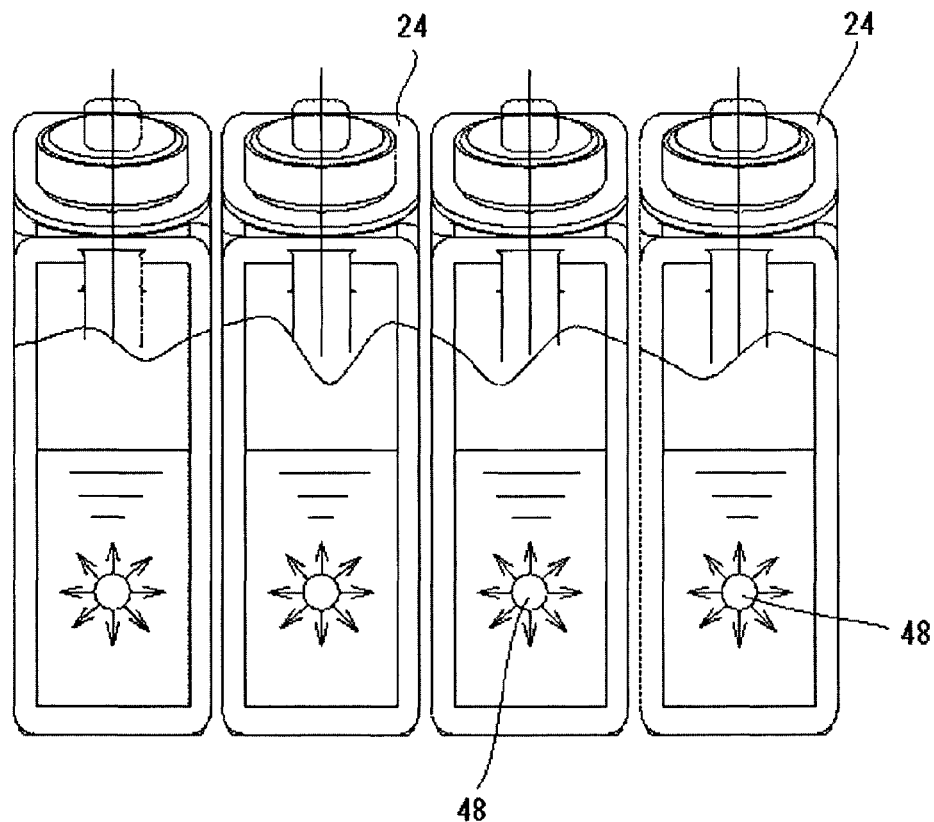
FIG. 2 is a diagram useful in explaining a state where a light projecting means is provided for each liquid chemical tank of the tissue fragment treatment apparatus depicted in FIG. 1.

As depicted in FIG. 2, the light-emitting diodes 48 are provided at positions near the bottom on one side out of the four side surfaces that form the side surfaces of the liquid chemical tanks 24 housed in the tank housing unit 14.

Figure 3:
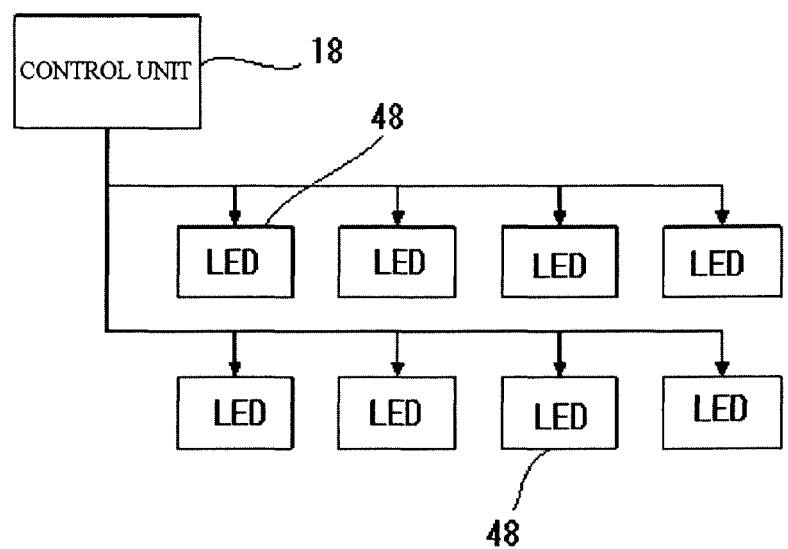
FIG. 3 is a block diagram useful in explaining control of the light-emitting diodes 48 provided for each liquid chemical tank 24.

ON-OFF switching of the light-emitting diodes 48 is controlled by the control unit 18 depicted in FIG. 3. The control unit 18 referred to here is the control unit 18 depicted in FIG. 6.

Note that the expression "LED" given in FIG. 3 means "light-emitting diode".

In this way, by providing the light-emitting diodes 48 near the bottom on one side of the liquid chemical tanks 24, light emitted by the light-emitting diodes 48 passes through the transparent plates 44 that cover the openings 42a in the center partition plate 42 and the resin walls on such side of the liquid chemical tanks 24 to become incident on the insides of the liquid chemical tanks 24. The incident light that is introduced into the liquid chemical tanks 24 is diffusely reflected within the liquid chemicals stored therein, resulting in the entire liquid chemicals appearing as if the chemicals are emitting light. This means that it is possible to visually check the amounts of liquid chemicals from outside the liquid chemical tanks 24, even from the other side (i.e., the door 14a side) of the liquid chemical tanks 24.

Also, as the door 14a, it is preferable to use a transparent door to make it possible to visually check the liquid chemical tanks 24 from one side of the liquid chemical tanks 24, and in particular, by using a colored transparent door as the door 14a, it is possible to further improve the contrast between the liquid chemical tanks 24 and the liquid chemicals that have been lit up by light emitted from the light-emitting diodes 48 and thereby make it even easier to visually check the amounts of the liquid chemicals.

Incidentally, since the refractive index of a liquid chemical is a value that is unique to such liquid chemical, the refractive index will differ between liquid chemicals. This means that when the liquid chemical in the liquid chemical tank 24 differs, the brightness and color will also differ due to differences in the refractive index for the light emitted from the light-emitting diodes 48. Accordingly, when the type of liquid chemical stored in a liquid chemical tank 24 differs to the liquid chemical that was originally planned for such liquid chemical tank 24, it will be easy to discover from the difference in brightness and/or color of the liquid chemical stored in the liquid chemical tank 24 for the light from the light-emitting diode 48 that a different liquid chemical is being stored. This means that accidents due to the use of different liquid chemicals can be prevented from the outset.

In addition, when treatment by the tissue fragment treatment apparatus has been carried out multiple times, resulting in a liquid chemical stored in a liquid chemical tank 24 having been used many times, there will be an increase in the proportions of other liquid chemicals that are mixed in. In such case also, based on changes in the brightness and color of the liquid chemical stored in the liquid chemical tank 24 for the light from the light-emitting diodes 48, it is possible to know that the concentration of the liquid chemical has changed due to the increase in the proportions of other liquid chemicals.

Also, as the number of uses of a liquid chemical stored in a liquid chemical tank 24 increases, the liquid chemical will become cloudy due to constituents and the like of tissue fragments becoming mixed in, which results in a fall in the contrast between the liquid chemical tank 24 and the liquid chemical for the light from the light-emitting diode 48. This means that the user will be able to easily know the usage limit of the liquid chemical from the extent to which the contrast between the liquid chemical tank 24 and the liquid chemical has fallen, and by taking suitable action such as replacing the liquid chemical, it is possible to favorably maintain the quality of the treated tissue fragment.

Note that by placing a float that blocks light from the light-emitting diode 48 inside a liquid chemical tank 24 that stores a liquid chemical where changes in concentration need to be managed even more precisely, it is possible to confirm the extent to which the float sinks from outside the liquid chemical tank 24 and thereby know the concentration of the liquid chemical.

In addition, when a red light-emitting diode, a green light-emitting diode, or a blue light-emitting diode is used as the light-emitting diode 48, all of the liquid chemical in a liquid chemical tank 24 will be brightly illuminated in a predetermined color by the light emitted by the light-emitting diode 48. This means that by providing light-emitting diodes 48 that emit light of colors that correspond to the types of liquid chemicals stored in the respective liquid chemical tanks 24, it is possible to easily manage the amount of each type of liquid chemical from outside the liquid chemical tanks 24 on a chemical-by-chemical basis.

Figure 4:
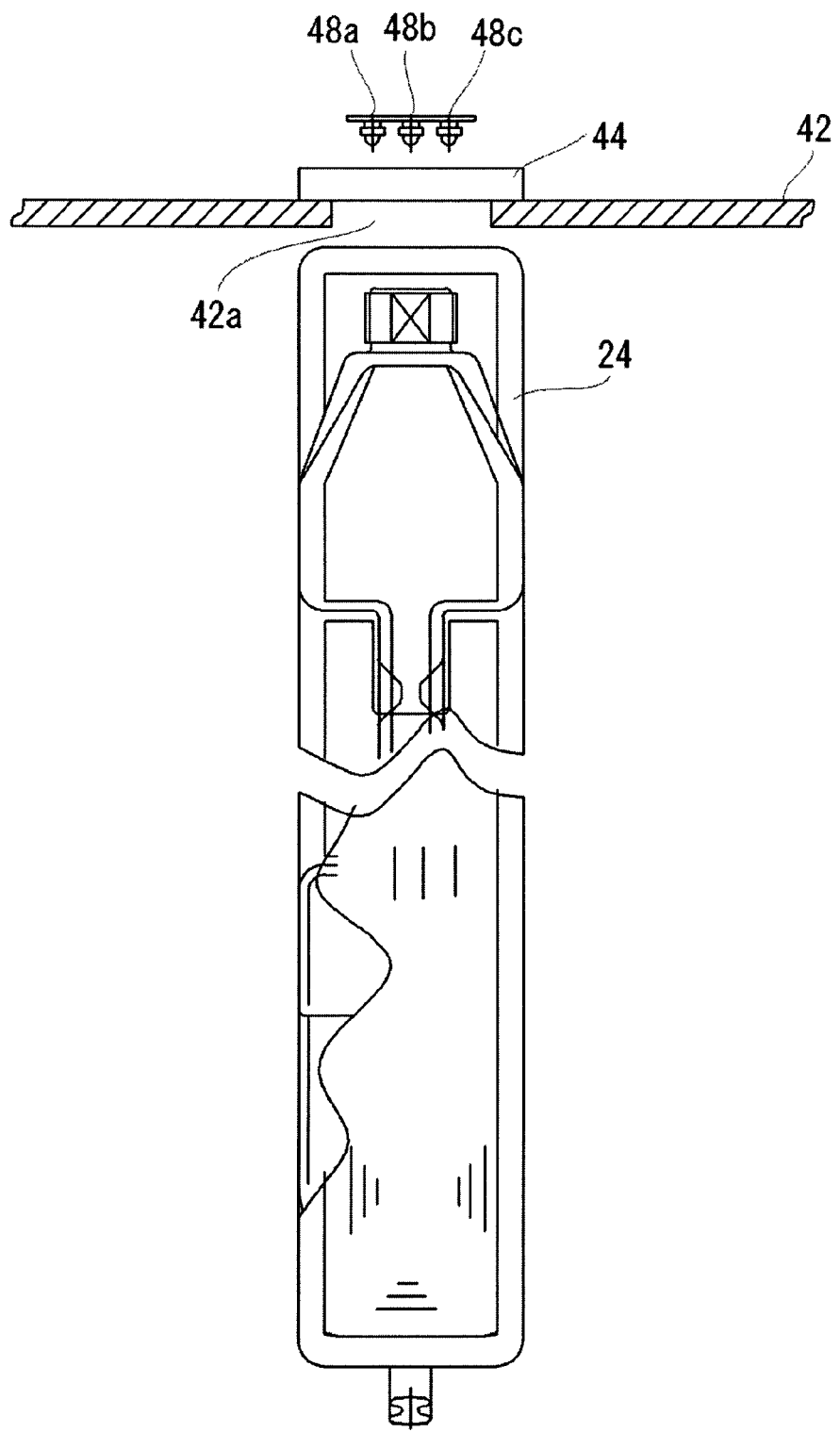
FIG. 4 is a diagram useful in explaining another example of a light projecting means provided at one end of the liquid chemical tanks 24.

Also, as depicted in FIG. 4, by providing a red light-emitting diode 48a, a green light-emitting diode 48b, and a blue light-emitting diode 48c on one side of a liquid chemical tank 24 and by controlling the amount of light emitted by the respective light-emitting diodes using the control unit 18 (see FIG. 6), it is possible to illuminate the liquid chemical tank 24 with light of a predetermined color. This means that by providing the red light-emitting diode 48a, the green light-emitting diode 48b, and the blue light-emitting diode 48c individually for the liquid chemical tanks 24, for example, and changing the combination of light-emitting diodes using the control unit 18, it is possible to change the projected light to a variety of colors.

For example, by controlling the red light-emitting diodes 48a, the green light-emitting diodes 48b, and the blue light-emitting diodes 48c provided for the respective liquid chemical tanks 24 so that a group of liquid chemical tanks composed of the liquid chemical tanks 24 that store the same liquid chemical are illuminated with light of the same color and liquid chemical tanks 24 that store different liquid chemicals are illuminated with light of respectively different colors, it will be possible for the user to easily visually check the amount of each liquid chemical stored inside the liquid chemical tanks 24 on a chemical-by-chemical basis. It is also possible for the user to check the connected state of the respective liquid chemical tanks 24 and to reliably know whether there is a liquid chemical tank that has exceeded a limit on the number of uses.

It is also possible to use light-emitting apparatuses in which the red light-emitting diode 48a, the green light-emitting diode 48b, and the blue light-emitting diode 48c are incorporated.

Here, although the light-emitting diodes 48 are provided separately as light-emitting means for the liquid chemical tanks 24 in the tissue fragment treatment apparatus depicted in FIG. 1 to FIG. 4, an integrated device in which a plurality of light-emitting diodes 48 are integrated may be provided on one side of a plurality of light-emitting diodes 48.

Also, although the light-emitting diodes 48 are provided near the bottom on one side of the liquid chemical tanks 24 in the tissue fragment treatment apparatus depicted in FIG. 1 to FIG. 4, it is also possible to provide light-emitting means such as light-emitting diodes on a plurality of sides (such as two sides) of the liquid chemical tanks 24.

In addition, at least two out of the red light-emitting diode 48a, the green light-emitting diode 48b, and the blue light-emitting diode 48c may be combined.

Figure 5:
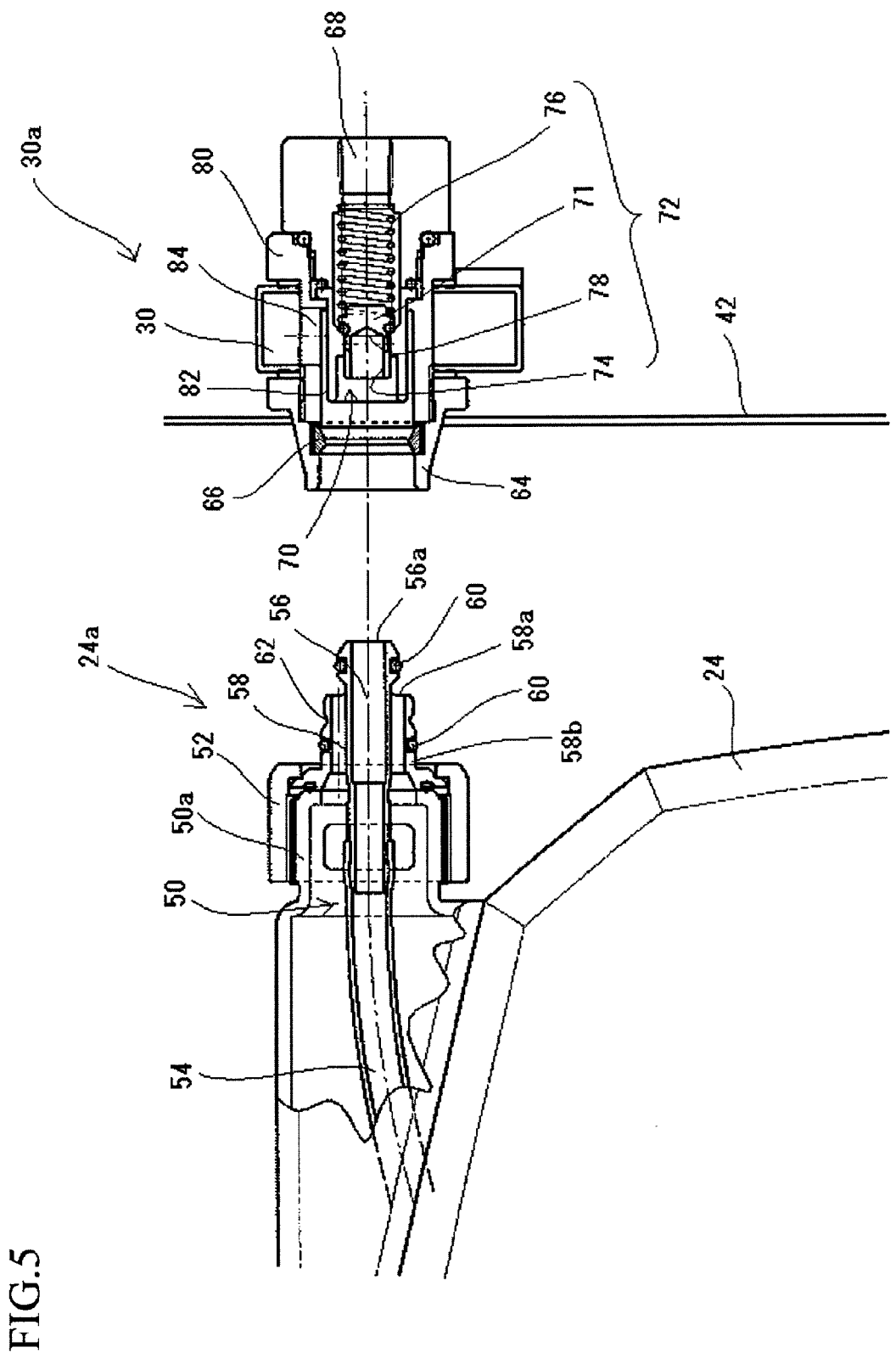
FIG. 5 is a partial cross-sectional view useful in explaining the construction of the connection plug provided on a liquid chemical tank and a connection socket fixed to a center partition plate.

The connection plugs 24a of the liquid chemical tanks 24 depicted in FIG. 1 are connected by a one-touch operation to the connection sockets 30a fixed to the center partition plate 42. As depicted in FIG. 5, each connection plug 24a includes an attachment portion 52 that has a screw thread formed on an inner wall thereof for attachment to an outer circumferential wall 50a of a supply opening 50, a liquid chemical conduit 56 that is connected to a supply tube 54 and allows the liquid chemical to flow therethrough, and a waste gas conduit 58 that allows gas to flow therethrough to enable gas produced inside the liquid chemical tanks 24 to be discharged. The waste gas conduit 58 is disposed outside the liquid chemical conduit 56 in the radial direction.

An outlet end portion 56a that is a front end portion of the liquid chemical conduit 56 is formed so as to protrude out further than an outlet end portion 58a that is a front end portion of the waste gas conduit 58. For this reason, the waste gas conduit 58 is formed with a larger diameter than the liquid chemical conduit 56.

The connection plug 24a is attached to the outer circumferential wall 50a of the supply opening 50 by screwing on the attachment portion 52.

O rings 60 used as seals are attached to an outer circumferential wall of the outlet end portion 56a of the liquid chemical conduit 56 and an outer circumferential wall 58b on the outside of the waste gas conduit 58. This means that when a connection plug 24a is connected to a connection socket 30a, it is possible to prevent leaks of liquid or gas from the gap between the connection plug 24a and the connection socket 30a.

In addition, a groove 62 is formed in the circumferential direction in the outer circumferential wall on the outside of the waste gas conduit 58. The groove 62 is used as a locking mechanism, described later.

Each connection socket 30a to be connected to a connection plug 24a has an insertion hole portion 64, into which the connection plug 24a is inserted, fixed to the center partition plate 42. The inner diameter of the insertion hole portion 64 is formed so that the connection plug 24a can be inserted as far as the outer circumferential wall on the outside of the waste gas conduit 58 of the connection plug 24a. A C-shaped ring 66 that is molded so as to protrude further inward than the inner circumferential surface of the insertion hole portion 64 is provided inside the insertion hole portion 64. Although the C-shaped ring 66 is formed with a diameter that will normally protrude further inward than the inner circumferential surface of the insertion hole portion 64, when the connection plug 24a has been inserted, the C-shaped ring 66 will widen outward and then fit inside the groove 62 of the connection plug 24a, thereby preventing the connection plug 24a from slipping out.

Also, a liquid chemical pipe 68 that is connected to the delivery pipe 28 (see FIG. 7) includes a cylindrical insertion portion 70 with a diameter that enables the liquid chemical conduit 56 of the connection plug 24a to be inserted and a check valve 72 that opens a conduit between the liquid chemical conduit 56 and the liquid chemical pipe 68 when pressed by the front end portion of the inserted liquid chemical conduit 56. The check valve 72 includes a valve element 71 that is energized by a spring 76 toward the insertion portion 70 inside the liquid chemical pipe 68 and a cylindrical pressing portion 74 that is integrally formed with the valve element 71 and contacts the front end portion of the inserted liquid chemical conduit 56 of the connection plug 24a. A concave portion 78 is formed in the insertion portion 70-side surface of the valve element 71. Since the check valve 72 is provided, if the connection socket 30a is not attached to a connection plug 24a, the liquid chemical pipe 68 will be closed due to the valve element 71 contacting the inner circumferential surface of a narrowed portion formed in the liquid chemical pipe 68, thereby preventing leaking and dripping for the liquid chemical.

A housing 80, which covers the insertion portion 70 with a gap 82 of a predetermined distance in between, and the waste gas header 30 are also provided outside the insertion portion 70. A waste gas pipe that connects to the waste gas conduit 58 of the connection plug 24a is formed by the gap 82 between the outer wall of the insertion portion 70 and the inner wall of the housing 80 and a through-hole 84 that is provided on a side surface of the housing 80 so as to connect the gap 82 and the waste gas header 30.

The connection plug 24a provided on the liquid chemical tank 24 and the connection socket 30a can be connected by pressing the connection plug 24a inside the connection socket 30a against the energizing force of the spring 76 so that the C-shaped ring 66 provided on the connection socket 30a becomes fitted inside the groove 62 of the connection plug 24a, thereby locking the connection.

On the other hand, when disconnecting the connection plug 24a provided on the liquid chemical tank 24 and the connection socket 30a, by pulling out the connection plug 24a, the locking of the C-shaped ring 66 and the groove 62 is released, making it possible to replace the liquid chemical tank 24 with a new liquid chemical tank 24.

Although the tissue fragment treatment apparatus described above has been applied to predetermined treatment carried out on a tissue fragment as an analyte, it is also possible to apply the apparatus to treatments such as staining an analyte produced by applying a body fluid such as blood to a prepared slide.

What is claimed is:

1. An analyte treatment apparatus for treating an analyte collected from an organism comprising:
   a plurality of liquid chemical tanks individually storing a variety of liquid chemicals, wherein each of the plurality of liquid chemical tanks is made of a resin material;
   a housing unit, wherein the plurality of liquid chemical tanks are housed in the housing unit, the housing unit having an opening corresponding to a first side of a liquid chemical tank housed therein;
   a treatment unit configured for carrying out a treatment on an analyte by successively supplying liquid chemicals from respective ones of the liquid chemical tanks to the treatment unit;
   a colored transparent door coupled to the housing unit and located at an opposite second side with respect to the first side of the liquid chemical tanks from which light diffusely reflected at the first side or in the liquid chemical tank can be visualized;
   a light projecting means provided outside of the treatment unit and configured to project light through the opening in the housing unit into a liquid chemical tank housed in the housing unit; and
   a control unit configured to control an ON-OFF switching of the light projecting means.

2. An analyte treatment apparatus according to claim 1, wherein the analyte treatment apparatus is a tissue fragment treatment apparatus that is configured to successively supply respective ones of the liquid chemicals in the plurality of liquid chemical tanks to a treatment tank in which a tissue fragment for use as a microscope sample has been inserted.

3. An analyte treatment apparatus according to claim 1, wherein the light projecting means is configured to separately project light into respective ones of the plurality of liquid chemical tanks.

4. An analyte treatment apparatus according to claim 1, wherein the light projecting means is a light-emitting diode.

5. An analyte treatment apparatus according to claim 1, wherein the light projecting means is a variable color light projecting means capable of changing a color of emitted light, and the control unit controls the color of the emitted light of the variable color light projecting means.

6. An analyte treatment apparatus according to claim 5, wherein the variable color light projecting means is constructed of at least two of a red light-emitting diode, a green light-emitting diode, and a blue light-emitting diode.

7. An analyte treatment apparatus according to claim 1, wherein a float that blocks the light from the light projecting means is placed inside the liquid chemical tanks.

* * * * *

UNITED STATES PATENT AND TRADEMARK OFFICE
CERTIFICATE OF CORRECTION

PATENT NO. : 8,282,881 B2
APPLICATION NO. : 12/668014
DATED : October 9, 2012
INVENTOR(S) : Kenji Takahashi Page 1 of 1

It is certified that error appears in the above-identified patent and that said Letters Patent is hereby corrected as shown below:

On the Title Page, in Item [75], under Inventor, please delete "Chikuma" and insert --Chikuma-shi--.

Signed and Sealed this
Twenty-eighth Day of May, 2013

Teresa Stanek Rea
*Acting Director of the United States Patent and Trademark Office*